(12) United States Patent
Liou et al.

(10) Patent No.: US 10,918,474 B2
(45) Date of Patent: Feb. 16, 2021

(54) IMPLANTING DEVICE

(71) Applicant: INDUSTRIAL TECHNOLOGY RESEARCH INSTITUTE, Hsinchu (TW)

(72) Inventors: Yu-Bing Liou, Hsinchu (TW); Ming-Chia Yang, Taipei (TW); Hsin-Yi Hsu, Taoyuan (TW); Yun-Han Lin, Taichung (TW); Wei-Hong Chang, Linnei Township (TW); I-Jong Wang, Taipei (TW); Hsin-Hsin Shen, Zhudong Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 128 days.

(21) Appl. No.: 16/122,438

(22) Filed: Sep. 5, 2018

(65) Prior Publication Data

US 2019/0076234 A1 Mar. 14, 2019

Related U.S. Application Data

(60) Provisional application No. 62/556,549, filed on Sep. 11, 2017.

(30) Foreign Application Priority Data

Jun. 26, 2018 (TW) .............................. 107121930 A (51) Int. Cl.
*A61F 2/14* (2006.01)
*A61B 17/34* (2006.01)
*A61F 9/00* (2006.01)

(52) U.S. Cl.
CPC .......... *A61F 2/148* (2013.01); *A61B 17/3468* (2013.01); *A61F 2/142* (2013.01); *A61F 2/145* (2013.01); *A61F 9/0017* (2013.01)

(58) Field of Classification Search
CPC .. A61F 2/14; A61F 2/142; A61F 2/145; A61F 2/148; A61F 2/1662; A61F 2/1664;
(Continued)

(56) References Cited

U.S. PATENT DOCUMENTS

| 6,050,999 A | 4/2000 | Paraschac et al. |
| 7,476,398 B1 | 1/2009 | Doillon et al. |

(Continued)

FOREIGN PATENT DOCUMENTS

| CN | 1754512 A | 4/2006 |
| CN | 201404586 Y | 2/2010 |

(Continued)

OTHER PUBLICATIONS

Liu et al., "Fabrication of diamond tips by the microwave plasma chemical vapor deposition Technique", Journal of Vacuum Science & Technology B, vol. 12, 1994, pp. 1712-1715 (Total. No. pp. 5).

(Continued)

*Primary Examiner* — Robert A Lynch
(74) *Attorney, Agent, or Firm* — Birch, Stewart, Kolasch & Birch, LLP (57) ABSTRACT

An implanting device is used for implanting a membrane in a biological tissue. The implanting device includes a sleeve, a membrane storage element, an injection element and a bubble generating element. The membrane storage element is fixed at the sleeve. The injection element is inserted in the sleeve and the membrane storage element, and includes a capturing end and connecting end. The capturing end is for capturing the membrane and has a hole. The bubble generating element is connected to the connecting end, and is for providing a gas that is then outputted via the hole. By the rotation of the injection element, the capturing end extends straight out of the membrane storage element or retracts straight into the membrane storage element.

19 Claims, 10 Drawing Sheets

(58) Field of Classification Search
CPC .... A61F 2/1667; A61F 2/1678; A61F 9/0008; A61F 9/0017; A61F 9/007; A61B 17/3468
See application file for complete search history.

(56) References Cited

U.S. PATENT DOCUMENTS

| | | | |
|---|---|---|---|
| 7,883,520 | B2 | 2/2011 | Gaeckle et al. |
| 8,029,515 | B2 | 10/2011 | Shiuey |
| 8,470,029 | B2 | 6/2013 | Walter et al. |
| 8,540,727 | B2 | 9/2013 | Dishler et al. |
| 8,636,795 | B2 | 1/2014 | Torres et al. |
| 8,668,735 | B2 | 3/2014 | Nigam et al. |
| 9,662,123 | B2 | 5/2017 | Tally et al. |
| 2007/0123919 | A1 | 5/2007 | Schachar et al. |
| 2010/0057093 | A1* | 3/2010 | Ide ............... A61F 2/1662 606/107 |
| 2010/0069915 | A1 | 3/2010 | Shiuey |
| 2011/0166650 | A1 | 7/2011 | Busin |
| 2012/0123533 | A1 | 5/2012 | Shiuey |
| 2012/0226286 | A1 | 9/2012 | Weston et al. |
| 2013/0085567 | A1 | 4/2013 | Tan et al. |
| 2014/0012295 | A1 | 1/2014 | Muraine |
| 2014/0180013 | A1 | 6/2014 | Hanlon et al. |
| 2015/0066044 | A1* | 3/2015 | Woods ............ A61F 2/1672 606/107 |
| 2016/0015852 | A1 | 1/2016 | Liou et al. |
| 2017/0348512 | A1* | 12/2017 | Orr ............... A61B 5/6857 |

FOREIGN PATENT DOCUMENTS

| | | |
|---|---|---|
| CN | 202146342 U | 2/2012 |
| CN | 101969898 B | 9/2013 |
| CN | 203749683 U | 10/2014 |
| CN | 101495063 B | 4/2015 |
| CN | 105163696 A | 12/2015 |
| CN | 105266928 A | 1/2016 |
| CN | 106037891 A | 10/2016 |
| CN | 106890048 A | 6/2017 |
| DE | 10 2010 051 458 B4 | 5/2013 |
| EP | 2 111 821 A1 | 10/2009 |
| EP | 2 404 573 A1 | 1/2012 |
| EP | 2 224 881 B1 | 4/2014 |
| EP | 2 764 846 A1 | 8/2014 |
| KR | 10-2016-0078465 A | 7/2016 |
| TW | M406435 U | 7/2011 |
| TW | I572347 B | 3/2017 |
| WO | WO 2013/076723 A1 | 5/2013 |
| WO | WO 2015/069189 A1 | 5/2015 |

OTHER PUBLICATIONS

Chinese Office Action and Search Report for Chinese Application No. 201810801534.2, dated May 15, 2020.
Taiwanese Office Action and Search Report for Taiwanese Application No. 107121930, dated Apr. 18, 2019.

* cited by examiner

IMPLANTING DEVICE

This application claims the benefit of U.S. provisional application Ser. No. 62/556,549, filed Sep. 11, 2017 and the benefit of Taiwan application Serial No. 107121930, filed Jun. 26, 2018, the subject matters of which are incorporated herein by reference.

TECHNICAL FIELD

The disclosure relates in general to an implanting device, and more particularly to an implanting device capable of generating bubbles.

BACKGROUND

After a conventional implanting device captures a membrane, the membrane is in contact with the implanting device. Having been placed in a biological tissue, the implanting device is withdrawn from the biological tissue, and a device generating bubbles by means of a syringe is again placed in the biological tissue to fill in bubbles to flatten and position the biological tissue. However, while withdrawing the implanting device, due to the contact between the membrane and the implanting device, the membrane is moved along with the implanting device, resulting in dislocation and deformation of the position of the membrane and thus contrarily prolonging the time of a surgical operation and significantly increasing the risk of a surgery failure.

Therefore, the disclosure provides an implanting device for improving foregoing conventional issues.

SUMMARY

According to one embodiment, an implanting device is provided. The implanting device is for implanting a membrane in a biological tissue, and includes a sleeve, a membrane storage element, an injection element and a bubble generating element. The membrane storage element is fixed at the sleeve. The injection element is inserted in the sleeve and the membrane storage element, and includes a capturing end and a connecting end. The capturing end is for capturing the membrane and has a first hole. The bubble generating element is connected to the connecting end, and provides a gas that is then outputted via the first hole. By the rotation of the injection element, the capturing end extends straight out of the membrane storage element or retracts straight into the membrane storage element.

To better understand the above and other aspect of the disclosure, embodiments are described in detail with the accompanying drawings below.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Figure 1A:
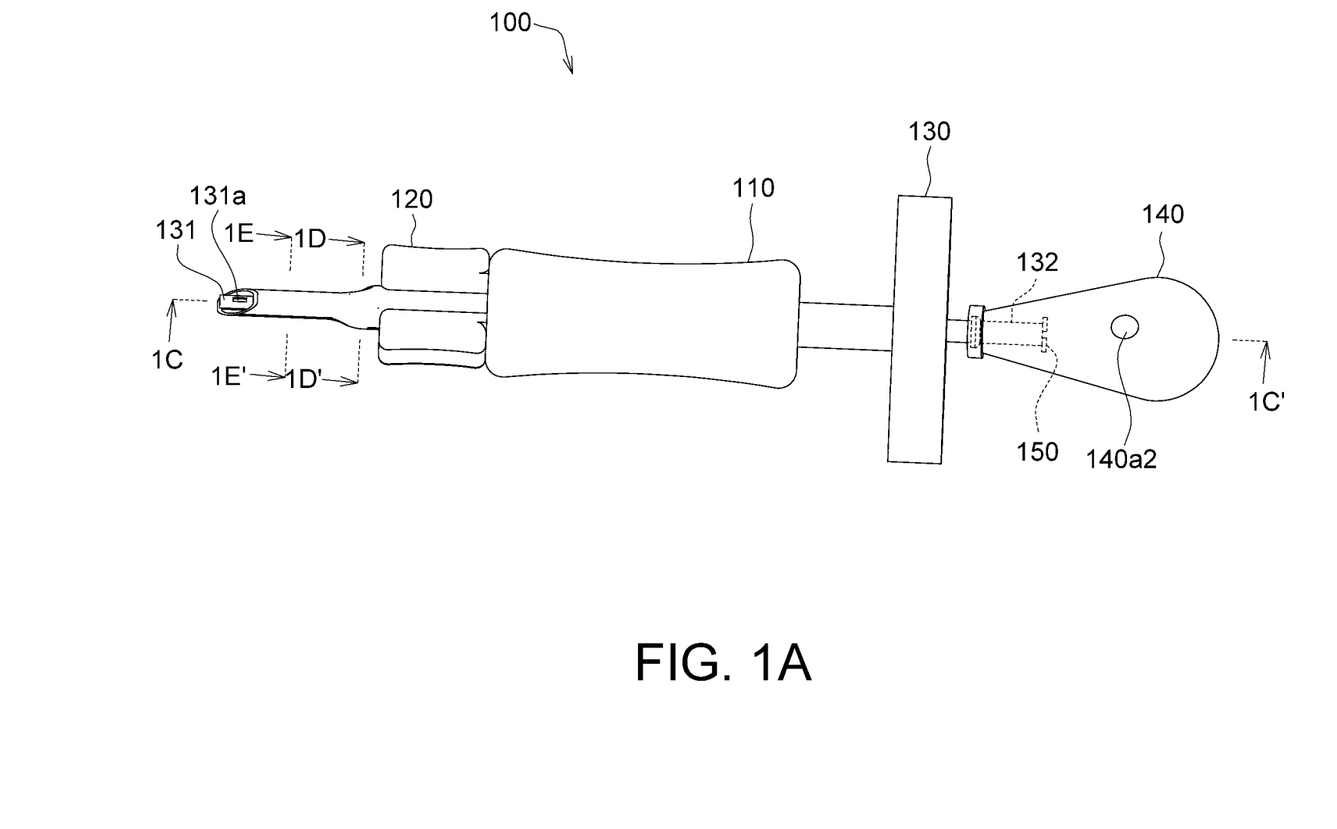
FIG. 1A is an appearance schematic diagram of an implanting device according to an embodiment.
Figure 1B:
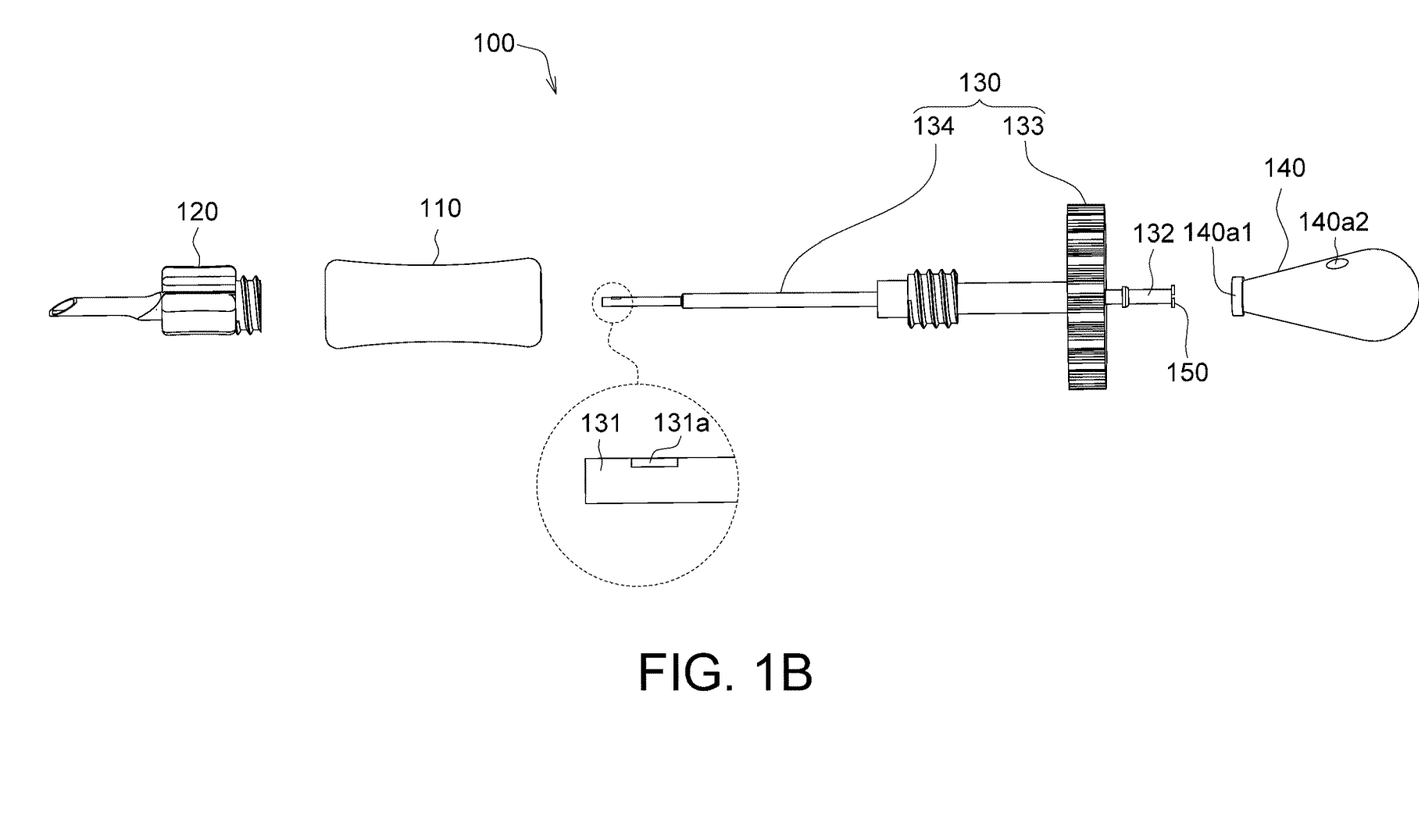
FIG. 1B is an exploded view of the implanting device in FIG. 1A.
Figure 1C:
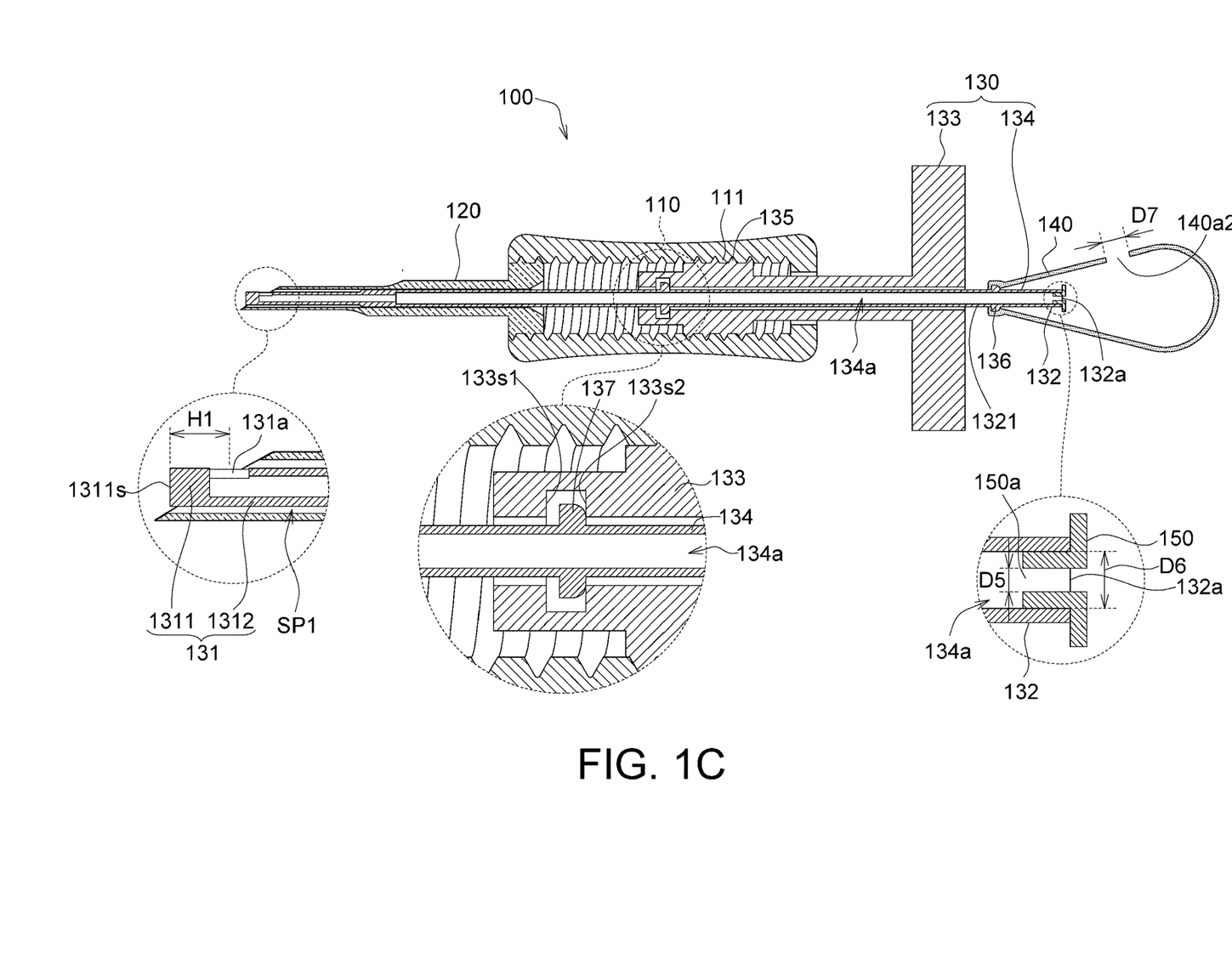
FIG. 1C is a section view of the implanting device in FIG. 1A along a direction 1C-1C'.
Figure 1D:
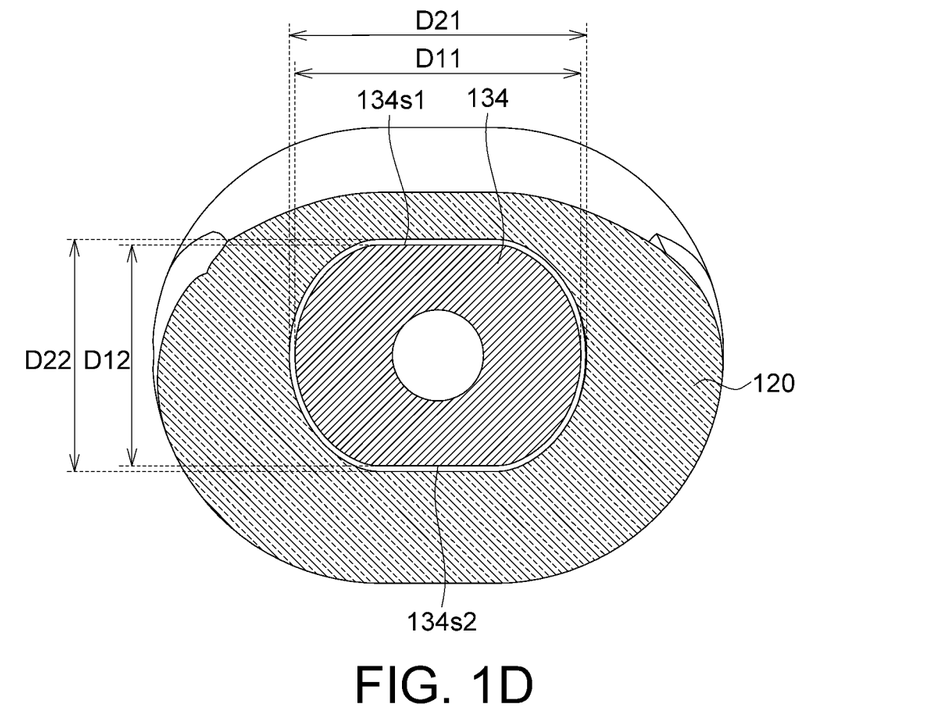
FIG. 1D is a section view of the implanting device in FIG. 1A along a direction 1D-1D'.
Figure 1E:
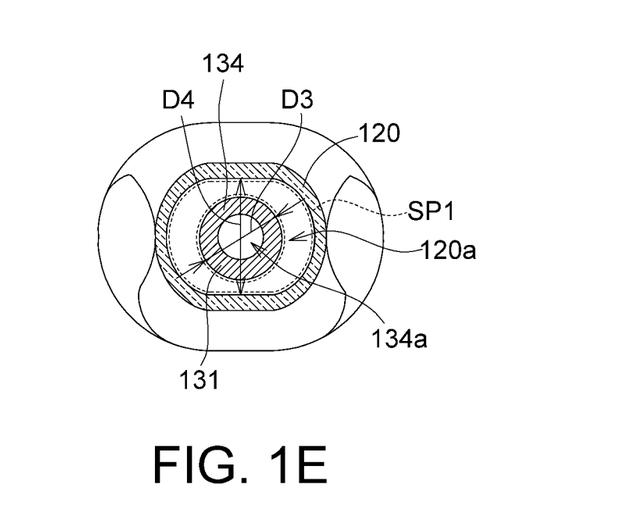
FIG. 1E is a section view of the implanting device in FIG. 1A along a direction 1E-1E'.

Referring to FIGS. 1A to 1E, FIG. 1A shows an appearance schematic diagram of an implanting device according to an embodiment, FIG. 1B shows an exploded view of the implanting device in FIG. 1A, FIG. 1C shows a section view of the implanting device in FIG. 1A along a direction 1C-1C', FIG. 1D shows a section view of the implanting device in FIG. 1A along a direction 1D-1D', and FIG. 1E shows a section view of the implanting device in FIG. 1A along a direction 1E-1E'.

The implanting device 100 is for implanting a membrane in a biological tissue. For example, the membrane is a corneal or a tissue repairing membrane, and the biological tissue is a tissue of a human body or an animal, such as an eye tissue or an internal organ tissue.

The implanting device 100 includes a sleeve 110, a membrane storage element 120, an injection element 130, a bubble generating element 140 and a non-return valve 150. The membrane storage element 120 is fixed at the sleeve 110. The injection element 130 is inserted in the sleeve 110 and the membrane storage element 120, and includes a capturing end 131 and a connecting end 132. The capturing end 131 is for capturing the membrane and has a first hole 131a. The bubble generating element 140 is connected to the connecting end 132, and provides a gas that is outputted via the first hole 131a. By the rotation of the injection element 130, the capturing end 131 is capable of extending straight out of the membrane storage element 120 or retracting straight into the membrane storage element 120.

Further, before implanting the membrane in the biological tissue, the injection element 130 can be rotated to allow the capturing end 131 to extend straight out of the membrane storage element 120 so as to capture the membrane. After having captured the membrane, the injection element 130 can be rotated to allow the capturing end 131 to retract straight into the membrane storage element 120 to store the membrane therein, so as to protect the membrane and prevent damage of the membrane during the subsequent process of the implanting device 100 entering the biological tissue. After the implanting device 100 is inserted in the biological tissue, the bubble generating element 140 can generate a gas, which is outputted via the first hole 131a to push the membrane to the biological tissue. In this embodiment, the bubble generating element 140 may be an air sac made of an elastic material such as rubber. Thus, by compressing the bubble generating element 140, the gas (e.g., air) in the bubble generating element 140 can be extruded into an injection channel 134a. In another embodiment, the bubble generating element 140 may be a pump or any other appropriate gas generating element or gas blowing element.

As shown in FIG. 1A, the number of the first hole 131a may be one or more than one. In an aspect of a geometric shape, the hole 131a is, for example, a polygonal hole, such as a rectangular hole, and may also be a circular hole, an ellipsoidal hole, a strip-shaped hole or a hole in other geometric shapes, given that a gas can be pushed therethrough and out the membrane. The number, geometric shape and/or opening area of the first hole 131a is not limited by the embodiments.

As shown in FIG. 1C, the capturing end 131 has an end wall 1311 and a first peripheral wall 1312. The first hole 131a penetrates the first peripheral wall 1312. In other words, the first hole 131a of the embodiment is provided at the first peripheral wall 1312 but not at the end wall 1311. Further, the membrane is usually hung on only the first peripheral wall 1312, and the first hole 131a is provided at the first peripheral wall 1312. Thus, the gas generated by the bubble generating element 140 can push the membrane hung on the first peripheral wall 1312 when the gas is outputted via the first hole 131a. Further, the end wall 1311 may be without any through hole structure, such that most of the gas generated by the bubble generating element 140 is outputted via the first hole 131a to achieve maximized gas output efficiency, allowing the membrane to disengage from the implanting device.

As shown in FIG. 1C and FIG. 1E, the membrane storage element 120 has a storage channel 120a, and an outer diameter D3 of the capturing end 131 of the injection element 130 is smaller than an inner diameter D4 of the storage channel 120a. Thus, the membrane may be stored in a storage space SP1 (a range defined by the dotted line) between the storage channel 120a and the capturing end 131 and be protected.

As shown in FIG. 1C, the injection element 130 has an injection channel 134a. The injection channel 134a extends from the connecting end 132 towards the capturing end 131, and is in communication with the first hole 131a, thus allowing the gas transported in the injection channel 134a to be outputted via the first hole 131a. Further, the injection channel 134a reveals a first opening 132a from the connecting end 132, such that the gas generated by the bubble generating element 140 can enter the injection channel 134a through the first opening 132a.

As shown in FIG. 1C, the injection element 130 includes a rotation portion 133 and a tube body 134. The tube body 134 has the capturing end 131, the connecting end 132 and the injection channel 134a described above. As shown, the tube body 134 is, for example, a straight tube, and the capturing end 131 and the connecting end 132 are two opposite ends of the straight tube. The tube body 134 and the membrane storage element 120 are made of, for example, a transparent material, so as to facilitate the observation of the state of the membrane 10. For example, because the tube body 134 and the membrane storage element 120 are transparent, the state of the membrane 10, e.g., the position and/or a curved state of the membrane 10, can be observed even if the membrane 10 is located inside the membrane storage element 120. In one embodiment, the membrane 10 may be colored to allow an operator to better observe the state of the membrane 10 through the color. In one embodiment, the tube body 134 and the membrane storage element 120 are made of, for example, plastic.

The injection channel 134a of the tube body 134 is in communication with an exterior terminal via the first hole 131a and the first opening 132a. Thus, most or even all of the gas generated by the bubble generating element 140 can enter via the first opening 132a, and most or even all of the gas can be outputted via the first hole 131a to achieve maximized gas output efficiency.

As shown in FIG. 1C, the injection element 130 includes a second flange 136, which protrudes from a second peripheral wall 1321 of the connecting end 132 of the tube body 134. The bubble generating element 140 closely covers the second flange 136 to seal the gap between the bubble generating element 140 and the second flange 136. Thus, the amount of the gas generated by the bubble generating element 140 and leaking from the gap can be minimized or even totally eliminated to achieve maximized gas output efficiency. In one embodiment, the second flange 136 and the tube body 134 may be an integrally formed structure; however, the disclosure is not limited thereto.

Further, the rotation portion 133 is rotatable relative to the sleeve 110 and is connected in a straightly movable manner to the sleeve 110. Further, as shown in FIG. 1C, the sleeve 110 has an inner thread 111, and the rotation portion 133 has an outer thread 135 screw matching the inner thread 111. Thus, with the thread movement, the rotation portion 133 and the sleeve 110 can rotate relatively and simultaneously move straight relatively.

Further, the tube body 134 is rotatable relative to the rotation portion 133 but is connected in a non-straightly movable manner to the rotation portion 133. Thus, when the rotation portion 133 rotates relative to the sleeve 110, the tube body 134 can rotate relative to the rotation portion 133, and the tube body 134 is driven by the rotation portion 133 and moves straight along with the rotation portion 133.

Further, as shown in FIG. 1C, the rotation portion 133 has a first stop wall $133s1$ and a second stop wall $133s2$ facing each other; the injection element 130 has a first flange 137, which is configured on the tube body 134 and located between the first stop wall $133s1$ and the second stop wall $133s2$ to confine the relative straight movements of the tube body 134 and the rotation portion 133. In other words, the first flange 137 is confined between the first stop wall $133s1$ and the second stop wall $133s2$, and the tube body 1334 is driven to simultaneously move straight when the rotation portion 133 moves straight. In one embodiment, the first flange 137 and the tube body 134 may be an integrally formed structure; however, the disclosure is not limited thereto. As shown in the diagram, although a margin exist between the first flange 137 and the first stop wall $133s1$, this margin does not affect the confinement of the first flange 137 between the first stop wall $133s1$ and the second stop wall $133s2$. In another embodiment, the margin between the first flange 137 and the first stop wall $133s1$ can be reduced or there may be no margin at all, i.e., the first flange 137 is fixed between the first stop wall $133s1$ and the second stop wall $133s2$.

As shown in FIG. 1D, the tube body 134 has an outer diameter D11 and a second outer diameter D12, wherein the first outer diameter D11 is greater than the second outer diameter D12. The membrane storage element 120 has a first inner diameter D21 and a second inner diameter D22, wherein the first inner diameter D21 is greater than the second inner diameter D22. The first outer diameter D11 matches the first inner diameter D21, and the second outer diameter D12 matches the second inner diameter D22. With the matching diameter in larger and smaller values, the relative rotation movements of the tube body 134 and the membrane storage element 120 can be restrained. In other words, when the rotation portion 133 rotates, even if the tube body 134 and the rotation portion 133 have a degree of freedom for relative movements, the tube body 134 is incapable of rotating relative to the rotation portion 133 due to the restriction of the larger and smaller diameters of the membrane storage element 120 but can only move straight relative to the membrane storage element 120. Thus, during a surgery, the position and angle of the first hole 131a do not change along with the rotation of the rotation portion 133.

As shown in FIG. 1D, the tube body 134 has a first plane 134s1 and a second plane 134s2 facing each other. The second outer diameter D12 is a distance between the first plane 134s1 and the second plane 134s2. The first plane 134s1 and the second plane 134s2 are, for example, two opposite sections of a cylinder. In another embodiment, the tube body 134 has an ellipsoidal section, wherein the length of the long axis of the ellipsoidal section is the first outer diameter D11 and the length of the short axis of the ellipsoidal section is the second outer diameter D12. However, given that the tube body 134 has two different outer diameters and the membrane storage element 120 has two different matching inner diameters, the geometric structures of the tube body 134 and the membrane storage element 120 are not limited by embodiments of the disclosure.

Further, as shown in FIG. 1C, the non-return valve 150 may be configured in the first opening 132a. For example, the non-return valve 150 may be a silicon plug that is partially plugged in the first opening 132a. The non-return valve 150 prevents back pressure and back waterflow. For example, the non-return valve 150 allows a gas G1 to enter the injection channel 134a but prohibits a tissue liquid of a biological tissue to exit the injection channel 134a. Taking the bubble generating element 140 as an air sac for instance, when the bubble generating element 140 is compressed, high pressure is formed in the bubble generating element 140 and the gas generated in the bubble generating element 140 is pushed into the injection channel 134a through the non-return valve 150; when the bubble generating element 140 is released, the pressure in the bubble generating element 140 is restored. With the non-return valve 150 configured, a tissue liquid of a biological tissue is prevented from being sucked into the injection channel 134a or flown out of the injection channel 134a through the non-return valve 150 when the pressure is restored. Thus, when the bubble generating element 140 is compressed next time, a tissue liquid in the injection channel 134a or flown out of the injection channel 134a is prevented from returning in the biological tissue, hence avoiding contamination of the biological tissue. Further, if the contamination issue is non-existent or the level of contamination is within a tolerable range, the non-return valve 150 may be omitted from the implanting device 100.

In one embodiment, the non-return valve 150 has a second hole 150a, which is located in the injection channel 134a. An inner diameter D5 of the second hole 150a is smaller than an inner diameter D6 of the first opening 132a. In one embodiment, the inner diameter D5 of the second hole 150a may be substantially equal to or smaller than 5 mm, so as to provide the foregoing technical effect of preventing back pressure and back waterflow.

Further, as shown in FIG. 1C, the bubble generating element 140 has a second opening 140a1 (shown in FIG. 1B) and a third hole 140a2. The bubble generating element 140 is mounted at the tube body 134 through the second opening 140a1. The third hole 140a2 provides a technical effect similar to that of the non-return vale 150, and associated details are omitted herein. Further, the third hole 140a2 is, for example, a circular hole, an ellipsoidal hole or a hole of other geometric shapes. Given that the foregoing technical effect of preventing back pressure and back waterflow is provided, the number, geometric shape and/or a configuration position of the third hole 140a2 are not limited by the embodiments.

When the bubble generating element 140 is separated from the tube body 134, the interior of the bubble generating element 140 is communication with the exterior through only the second opening 140a1 and the third hole 140a2. When the bubble generating element 140 is mounted at the tube body 134, because the second opening 140a1 is almost or entirely sealed, the interior of the bubble generating element 140 communicates with the exterior through only the third hole 140a2. Thus, when the bubble generating element 140 is compressed, the interior of the bubble generating element 140 generates a sufficiently high pressure to push the gas in the bubble generating element 140. Further, in one embodiment, an inner diameter D7 of the third hole 140a2 may be between approximately 0.5 mm and 1.5 mm, e.g., 1 mm. In another embodiment, if not needed, the third hole 140a2 may also be omitted from the bubble generating element 140. That is, when the bubble generating element 140 is separated from the tube body 134, the interior of the bubble generating element 140 communicates with the exterior through only the second opening 140a1.

Figure 2:
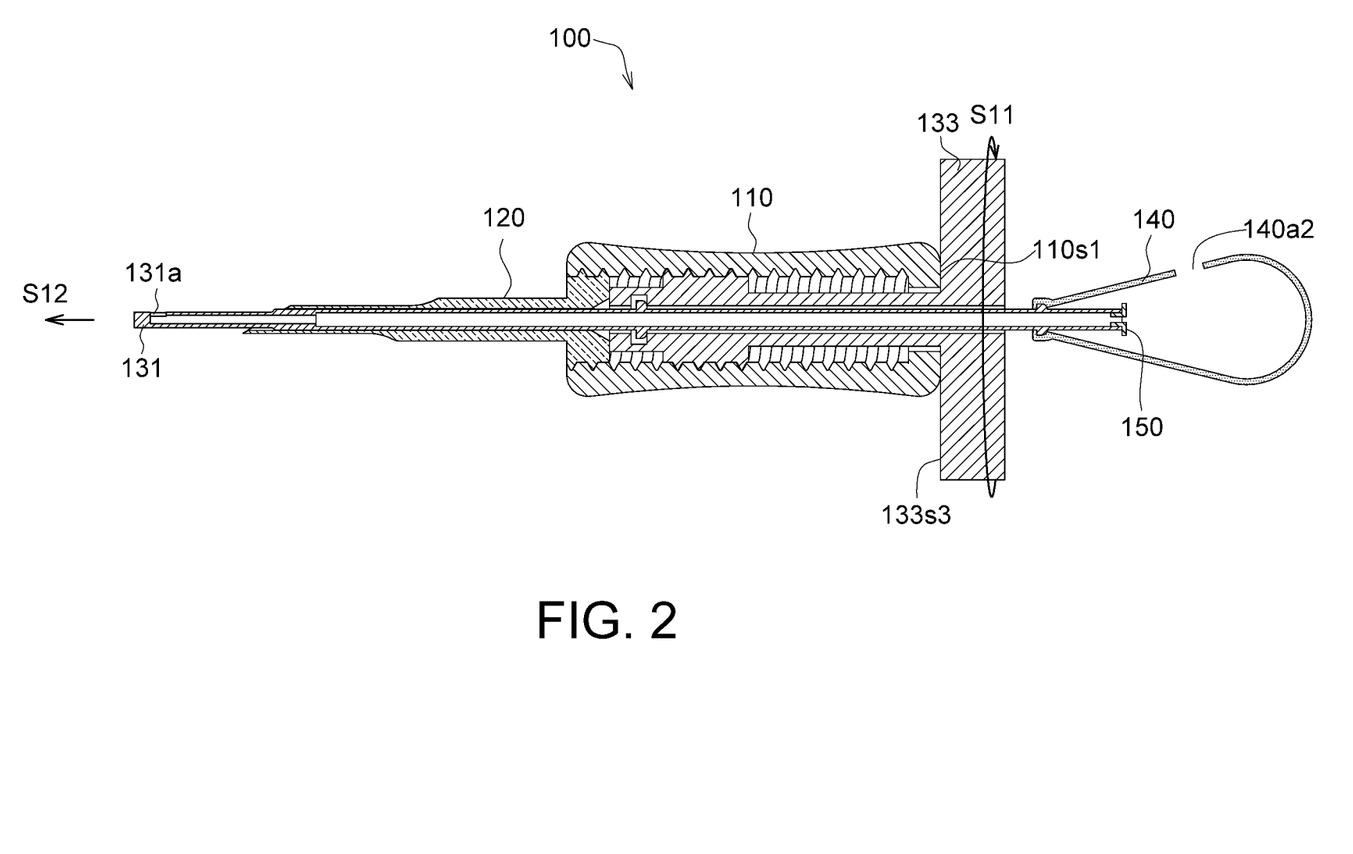
FIG. 2 is a schematic diagram of a capturing end of the implanting device in FIG. 1C extending out of a membrane storage element.
Figure 3:
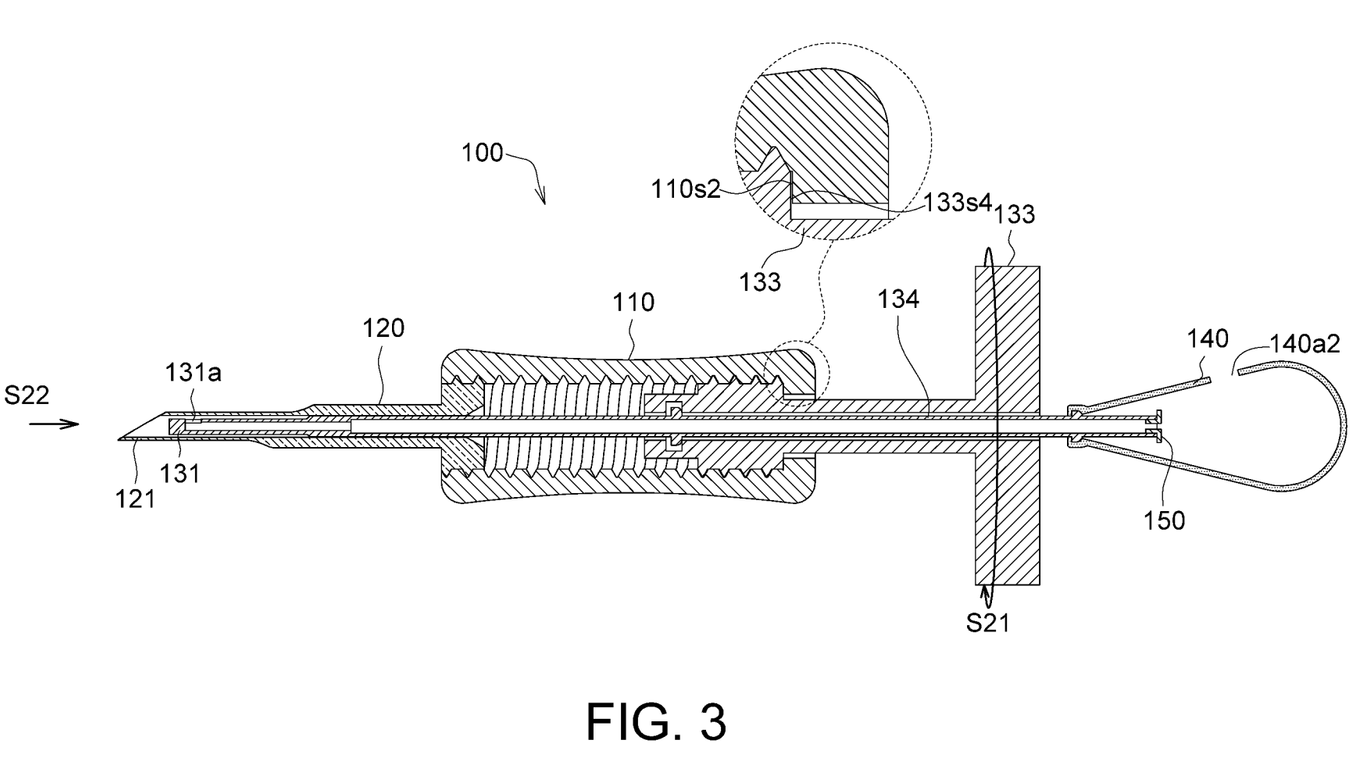
FIG. 3 is a schematic diagram of a capturing end of the implanting device in FIG. 1C retracting into a membrane storage element.

Referring to FIG. 2 and FIG. 3, FIG. 2 shows a schematic diagram of the capturing end 131 of the implanting device 100 in FIG. 1C extending out of the membrane storage element 120, and FIG. 3 shows a schematic diagram of the capturing end 131 of the implanting device 100 in FIG. 1C retracting into the membrane storage element 120.

As shown in FIG. 2, the rotation portion 133 rotates along a first rotation direction S11 to drive the tube body 134 to move straight towards an extension direction S12, such that the first hole 131a of the capturing end 131 is extended out of the membrane storage element 120 to readily capture the membrane. As shown in the drawings, the rotation portion 133 of the injection element 130 has a first outer end surface 133s3 located outside the sleeve 130, the sleeve 110 has a second outer end surface 110s1, the first outer end surface 133s3 faces the second outer end surface 110s1, and the first outer end surface 133s3 and the second outer end surface 110s1 determine a first extremum position of the injection element 130 relative to the sleeve 110, as the position shown in FIG. 2.

More specifically, when the rotation portion 133 rotates along the first rotation direction S11 relative to the sleeve 110, the rotation portion 133 simultaneously moves straight along the extension direction S12 through the thread movements until the first outer end surface 133s3 and the second outer end surface 110s1 are abuttingly connected. When the first outer end surface 133s3 and the second outer end surface 110s1 are abuttingly connected, the rotation portion 133 and the sleeve 110 are cannot rotate, and the position at this point is referred to as the first extremum position.

As shown in FIG. 3, the rotation portion 133 of the injection element 130 has a third outer end surface 133s4 located in the sleeve 130, the sleeve 110 has an inner end surface 110s2, the third outer end surface 133s4 faces the inner end surface 110s2, and the third outer end surface 133s4 and the inner end surface 110s2 determine a second extremum position of the injection element 130 relative to the sleeve 110, as the position shown in FIG. 3.

More specifically, when the rotation portion 133 rotates along a second rotation direction S21 relative to the sleeve 110, the rotation portion 133 simultaneously moves straight along a retraction direction S22 relative to the sleeve 110 until the third outer end surface 133s4 and the inner end surface 110s2 are abuttingly connected. When the third outer end surface 133s4 and the inner end surface 110s2 are abuttingly connected, the rotation portion 133 and the sleeve 110 cannot rotate, and the position at this point is referred to the second extremum position. The second rotation direction S21 and the first rotation direction S11 are two opposite directions.

As shown in FIG. 3, the membrane storage element 120 has an end portion 121. For example, the end portion 121 is a pointed end to help the implanting device 100 to insert with minimal effort into a biological tissue. Further, as shown in the drawing, a slanted section of the end portion 121 in a pointed end can provide the technical effect of allowing an operator to determine a facing direction of the first hole 131a. Thus, even if the first hole 131a is retracted in the membrane storage element 120 and is not revealed, the facing direction of the first hole 131a can still be determined through the slanted section of the pointed end, so as to help the operator to operate the implanting device 100 to enter at an appropriate angle (e.g., an upward facing direction of the first hole 131a) a biological tissue. Further, the first hole 131a in FIG. 3 may face upward and may also face downward, or may face any direction. Because the slanted section of the end portion 121 in a pointed end allows an operator to determine the facing direction of the first hole 131a, the determination made by the operator in regard to the position of the first hole 131a is unaffected regardless of the facing direction of the first hole 131a.

Figure 4:
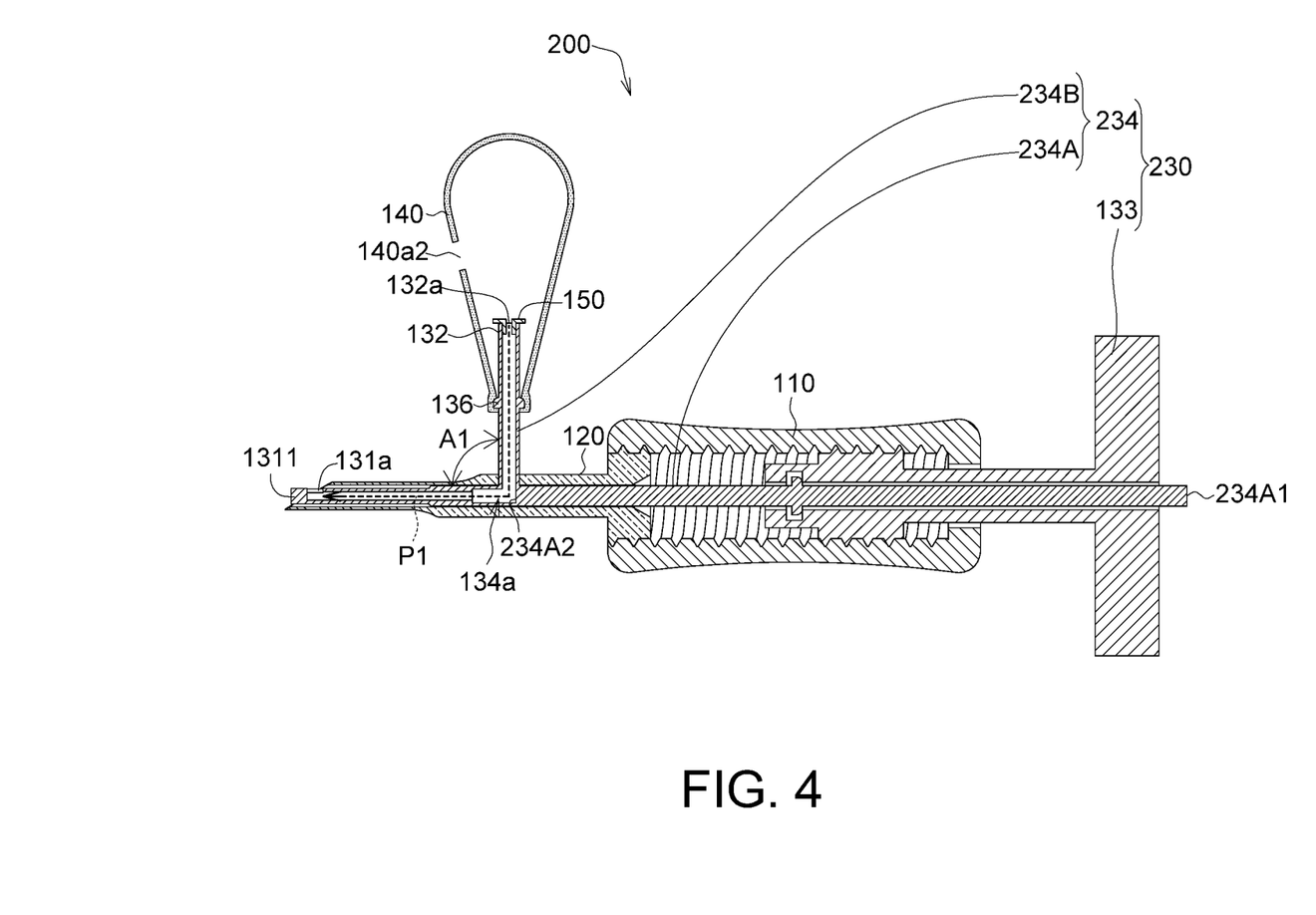
FIG. 4 is an appearance schematic diagram of an implanting device according to another embodiment.

FIG. 4 shows an appearance schematic diagram of an implanting device 200 according to another embodiment. The implanting device 200 includes a sleeve 110, a membrane storage element 120, an injection element 230, a bubble generating element 140 and a non-return valve 150. The implanting device 200 according to this embodiment has a similar to identical structure to the foregoing implanting device 100, and differs in that the structure of the injection element 230 of the implanting device 200 is different from that of the injection element 130.

More specifically, the injection element 230 includes a rotation portion 133 and a tube body 234. The tube body 234 includes a first tube 234A and a second tube 234B. The first tube 234A is insertingly provided in the rotation portion 133, the sleeve 110 and the membrane storage element 120. The second tube 234B is connected to the first tube 234A and is located outside the membrane storage element 120. The first tube 234A has a capturing end 131, an end portion 234A1, a part of an injection channel 134a and an inner end surface 234A2. The second tube 234B has a connecting end 132 and the other part of the injection channel 134a. For example, the first tube 234A is a straight tube, wherein the capturing end 131 and the end portion 234A1 are two opposite ends of the straight tube.

In this embodiment, the end portion 234A1 of the first tube 234A is, for example, a sealed end, such that the injection channel 134a of the first tube 234A communicates with the exterior through only the first hole 131a and the first opening 132a of the connecting end 132. Thus, most or even all of the gas generated by the bubble generating element 140 can enter via the first opening 132a, and most or even all of the gas can be outputted via the first hole 131a to achieve maximized gas output efficiency. Further, compared the position of the connecting end 132 in FIG. 1C, the position of the connecting end 132 of this embodiment is closer to the first hole 131a, so as to shorten a transportation path P1 between the first opening 132a and the first hole 131a to more quickly output the gas generated by the bubble generating element 140 via the first hole 131a. Further, due to the shortened gas transportation path P1, energy attenuation of the gas is reduced, allowing the gas to be outputted via the first hole 131a by a greater speed.

As shown in FIG. 4, the part between the inner end surface 234A2 and the end portion 234A1 is a physical material. Thus, the volume of the injection channel 134a is reduced to increase or maintain the gas pressure of the gas in the injection channel 134a, further allowing the gas to be outputted at an expected gas pressure via the first hole 131a.

As shown in FIG. 4, the second tube 234B and the first tube 234A intersect. For example, the second tube 234B and the first tube 234A are substantially perpendicularly connected; that is, an included angle A1 between the second tube 234B and the first tube 234A is between 90 and 180 degrees, e.g., 120 degrees, or is an acute angle. Further, the second tube 234B and the first tube 234A may be an integrally formed structure. In another embodiment, the first tube 234A and the second tube 234B may be formed separately, and then assembled together by means of screwing or fastening.

FIG. 5A to 5F show diagram of a process of the implanting device 100 in FIG. 1C performing corneal implantation.

Figure 5A:
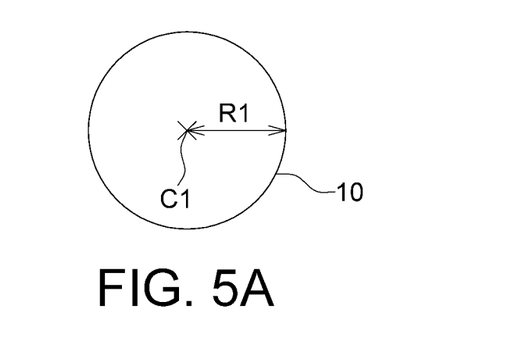
FIGS. 5A to 5F are diagram of a process of the implanting device in FIG. 1C performing corneal implantation.

As shown in FIG. 5A, a membrane 10, for example, a corneal, is provided, wherein the membrane 10 has a radius R1.

Figure 5B:
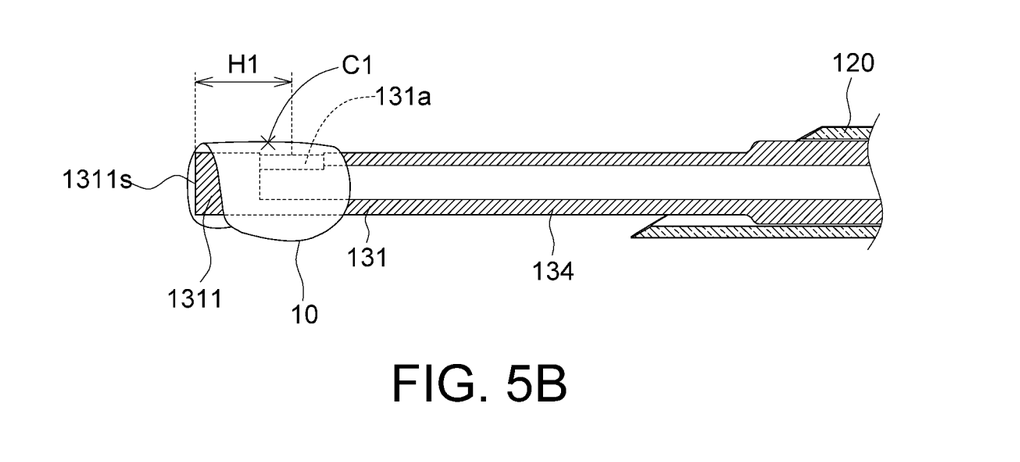

As shown in FIG. 5B, the membrane 10 is captured and provided in a state where the capturing end 131 is extended out relative to the membrane storage element 120. As shown in the diagram, the end wall 1311 of the capturing end (not shown in FIG. 4B) has an end surface 1311s, and a distance H1 between the center of the first hole 131a and the end surface 1311s is substantially equal to or greater than the radius of the membrane. Thus, when the center C1 of the membrane 10 hung at the capturing end 131 is substantially corresponding to the position of the first hole 131a, almost the entire membrane 10 is hung on the capturing end 131 to reinforce the stability of the membrane 10 (if the membrane 10 protrudes from the end surface 1311s, the probability that the membrane 10 falls off may be increased).

Figure 5C:
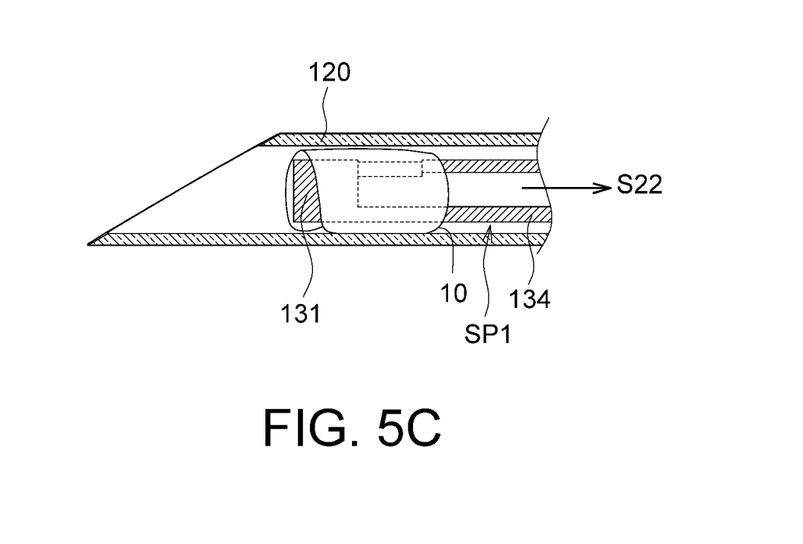

As shown in FIG. 5C, the rotation portion 133 is rotated to cause the tube body 134 to move straight along the retraction direction S22 until the capturing end 131 is retracted into the membrane storage element 120, so as to store the membrane 10 in the storage space SP1 and protect the membrane 10. Because the membrane storage element 120 is transparent, the state of the membrane 10, e.g., the position and/or a curved stated of the membrane 10, can be observed even if the membrane 10 is located inside the membrane storage element 120.

Figure 5D:
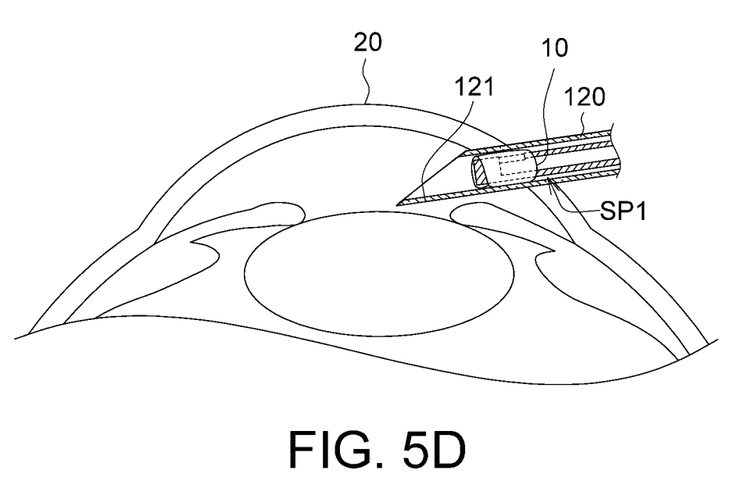

As shown in FIG. 5D, the end portion 121 of the membrane storage element 120 is inserted into a biological tissue 20, e.g., into an eyeball. As the membrane 10 is stored in the storage space SP1 in the membrane storage element 120, the membrane 10 is not damaged due to contact with the biological tissue 20 during the process that the membrane storage element 120 enters the biological tissue 20.

Figure 5E:
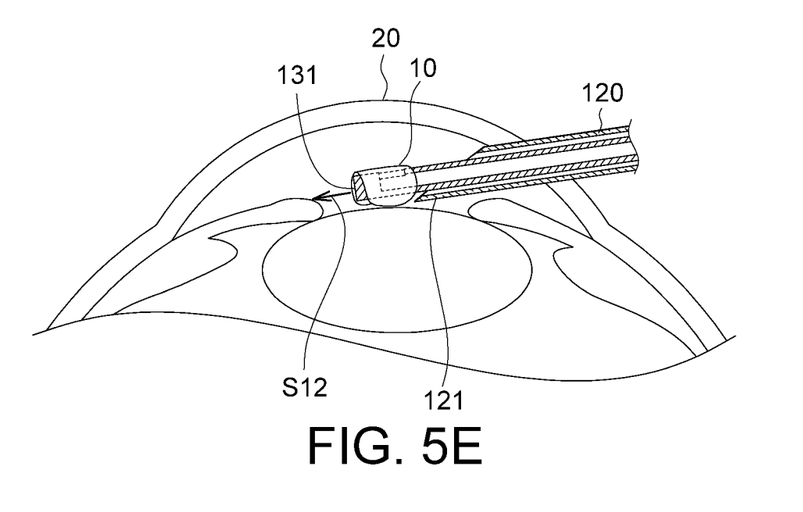

As shown in FIG. 5E, the rotation portion 133 is rotated to cause the tube body 134 to move straight along the extension direction S12 until the capturing end 131 is extended out from the membrane storage element 120, so as to forward the membrane 10 into the biological tissue 20, e.g., to an anterior chamber of the eyeball.

Figure 5F:
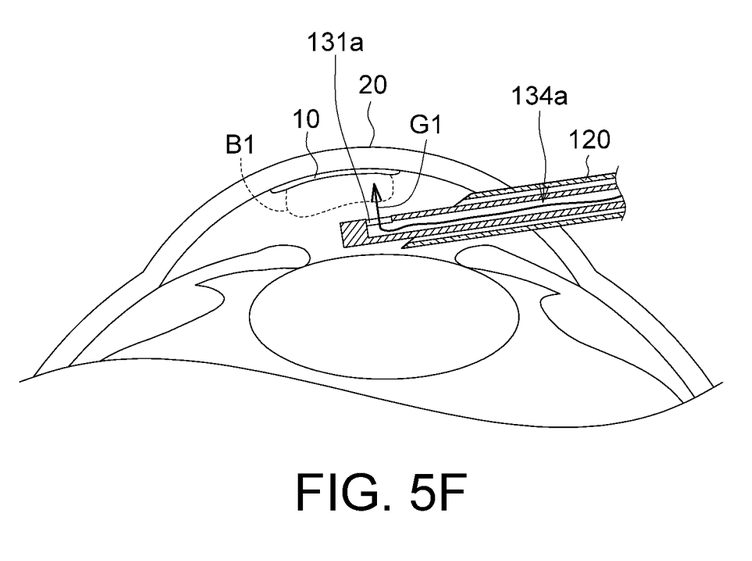

As shown in FIG. 5F, the bubble generating element 140 generates the gas G1, which enters the injection channel 134a and is outputted via the first hole 131a. The gas G1 may form a bubble B1 in a tissue liquid of the anterior chamber, and the bubble B1 pushes the membrane 10 upward and out such that the membrane 10 is completely disengaged from the implanting device 100. More specifically, the bubble B1 can spread and flatten the membrane 10 in a curved state, and the flattened membrane 10 can better receive the buoyant force from the bubble B1 and be pushed upwards, such that the membrane 10 is completely disengaged from the implanting device 100.

Next, the implanting device 100 is withdrawn from the biological tissue 20. As the membrane 10 is completely disengaged from the implanting device 100, the implanting device 100 does not interfere the position of the membrane 10 during the process that the implanting device 100 withdraws from the biological tissue 20, hence increasing the rate of a successful surgery.

In a conventional implanting surgery completed by two implanting devices, a membrane placed in can easily cause dislocation of a corneal due to a pressure difference inside and outside an eye when the two implanting devices are withdrawn, resulting in difficulties in tissue positioning. Compared to such conventional solution, according to embodiments of the disclosure, only one implanting device 100 is needed to complete an implanting surgery, hence preventing the problem of the pressure difference inside and outside an eye from reducing the rate of a successful surgery.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An implanting device, adapted to place a membrane in a biologic tissue, the implanting device comprising:
   a sleeve;
   a membrane storage element, fixed at the sleeve;
   an injection element, inserted in the sleeve and the injection element, comprising a capturing end and a connecting end, the capturing end for capturing the membrane and having a first hole; and
   a bubble generating element, connected to the connecting end, for providing a gas that is outputted via the first hole;
   wherein the capturing end, by rotation of the injection element, extends straight out of the membrane storage element or retracts straight into the membrane storage element;
   wherein the injection element has a first outer diameter and a second outer diameter, and the first outer diameter is greater than the second outer diameter; the membrane storage element has a first inner diameter and a second inner diameter, and the first inner diameter is greater than the second inner diameter; the first outer diameter matches the first inner diameter, and the second outer diameter matches the second inner diameter.

2. The implanting device according to claim 1, wherein the injection element comprises:
   a rotation portion, rotatable relative to the rotation portion and connected in a straightly movable manner to the rotation portion; and
   a tube body, rotatable relative to the sleeve and connected in a non-straightly movable manner to the sleeve.

3. The implanting device according to claim 2, wherein the sleeve has an inner thread, and the rotation portion has an outer thread screw matching the inner thread.

4. The implanting device according to claim 2, wherein the rotation portion has a first stop wall and a second stop wall facing each other, the injection element has a first flange, the first flange is configured on the tube body and is located between the first stop wall and the second stop wall, so as to confine relative straight movements of the tube body and the rotation portion.

5. The implanting device according to claim 2, wherein the tube body has an injection channel, and the injection channel extends from the connecting end towards the capturing end communicates with the first hole.

6. The implanting device according to claim 5, wherein the tube body comprises the connecting end and the first hole, the connecting end has a first opening, and the injection element communicates with an exterior through the first hole and the first opening.

7. The implanting device according to claim 1, wherein the injection element has a first plane and a second plane facing each other, and the second outer diameter is a distance between the first plane and the second plane.

8. The implanting device according to claim 1, wherein the injection element has a first outer end surface located outside the sleeve, the sleeve has a second outer end surface, the first outer end surface faces the second outer end surface, and the first outer end surface and the second outer end surface determine a first extremum position of the injection element relative to the sleeve.

9. The implanting device according to claim 1, wherein the injection element has a third outer end surface located inside the sleeve, the sleeve has an inner end surface, the third outer end surface faces the inner end surface, and the third outer end surface and the inner surface determine a second extremum position of the injection element.

10. The implanting device according to claim 1, wherein the capturing end comprise a first peripheral wall, and the first hole penetrates the first peripheral wall.

11. The implanting device according to claim 1, wherein the capturing end has an end surface, and a distance between the first hole and the end surface is substantially equal to or greater than a radius of the membrane.

12. The implanting device according to claim 1, wherein the first hole is a strip-shaped hole or a circular hole.

13. The implanting device according to claim 1, wherein a quantity of the first hole is one.

14. The implanting device according to claim 1, wherein the injection element has a second flange, the second flange protrudes from a second peripheral wall of the connecting end of the injection element, and the bubble generating element covers the second flange.

15. The implanting device according to claim 1, wherein the membrane storage element has a storage channel, an outer diameter of the capturing end of the injection element is smaller than an inner diameter of the storage channel, and a space between the storage channel and the capturing end is for storing the membrane.

16. The implanting device according to claim 1, wherein the injection element comprise a first tube and a second tube, the first tube is located in the sleeve and the membrane storage element and has the capturing end disposed on the first tube, and the second tube is connected to the first tube and located outside the membrane storage element and has the connecting end disposed on the second tube.

17. The implanting device according to claim 16, wherein the first tube and the second tube are substantially perpendicularly connected.

18. The implanting device according to claim 1, further comprising:

a non-return valve, configured at a first opening of the connecting end, having a second hole, wherein an inner diameter of the second hole is smaller than an inner diameter of the first opening;

wherein the non-return valve allows the gas to enter the injection channel.

19. The implanting device according to claim 1, wherein the bubble generating element has a second opening and a third hole, the second opening is connected to the connecting end, and the bubble generating element communicates with an exterior through the third hole.

\* \* \* \* \*